Figure 1:
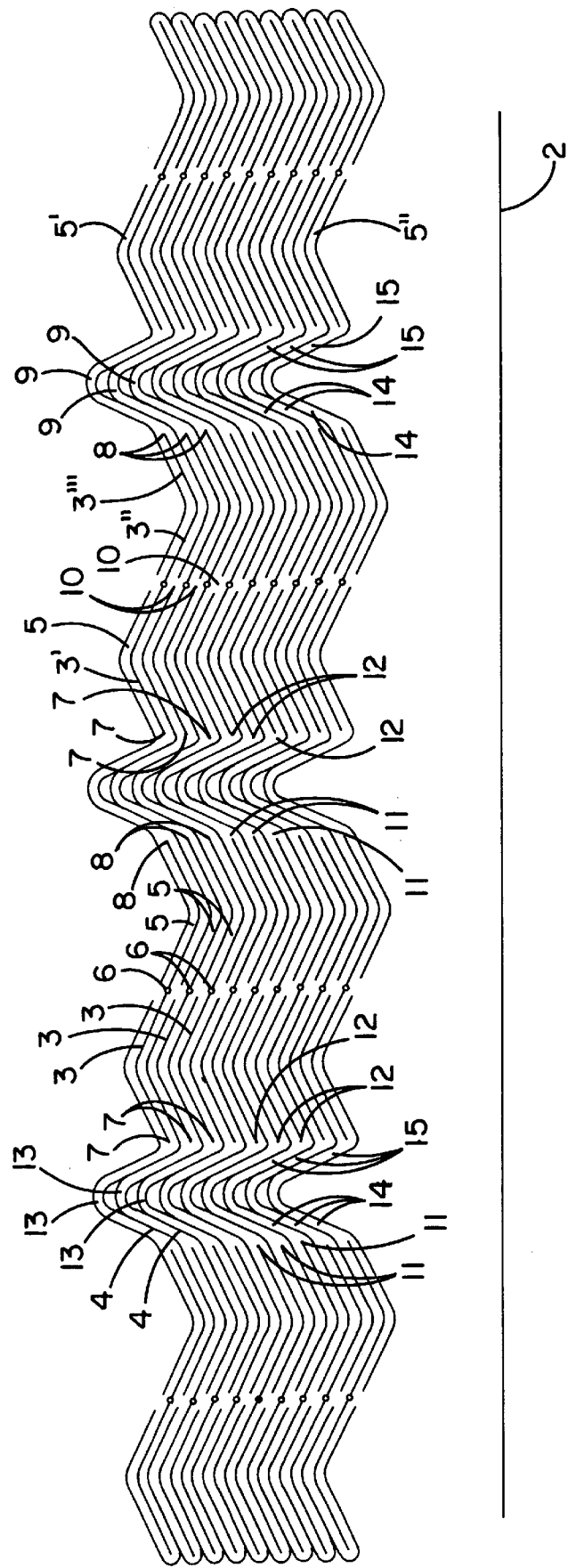

United States Patent
Starck et al.

[11] Patent Number: 5,876,449
[45] Date of Patent: Mar. 2, 1999

[54] STENT FOR THE TRANSLUMINAL IMPLANTATION IN HOLLOW ORGANS

[75] Inventors: Erhard Starck, Kronberg; Rainer Trapp, Graben-Neudorf, both of Germany

[73] Assignee: Variomed AG, Liechtenstein

[21] Appl. No.: 624,294

[22] Filed: Mar. 29, 1996

[30] Foreign Application Priority Data

| Apr. 1, 1995 | [DE] | Germany | 195 12 066.3 |
| May 7, 1995 | [DE] | Germany | 195 16 191.2 |
| Oct. 30, 1995 | [DE] | Germany | 195 40 851.9 |

[51] Int. Cl.[6] .................................. A61F 2/06; A61F 2/04
[52] U.S. Cl. .................................. 623/12; 623/1
[58] Field of Search .................... 623/1, 11, 12; 606/194, 195, 198

[56] References Cited

U.S. PATENT DOCUMENTS

| 4,776,337 | 10/1988 | Palmaz ........................................ 623/1 |
| 4,994,071 | 2/1991 | MacGregor ............................. 606/194 |
| 5,139,480 | 8/1992 | Hickle et al. . |
| 5,366,504 | 11/1994 | Andersen et al. ........................... 623/1 |
| 5,496,365 | 3/1996 | Sgro ........................................ 623/11 |

FOREIGN PATENT DOCUMENTS

| 0 335 341 A1 | 10/1989 | European Pat. Off. . |
| 0 566 807 A1 | 10/1993 | European Pat. Off. . |
| 43 03 181 A1 | 8/1994 | Germany . |
| 2 281 865 | 3/1995 | United Kingdom . |

OTHER PUBLICATIONS

G.M. Richter, "Theorestische Grundlagen des ballonexpandierbaren Palmaz–Stents", pp. 50–55.
K. Rauber et al., "Experimentelle Erfahrungen mit Nitinol–Prothesen", pp. 65–70.
W.J. Van Der Giessen, M.D. et al., "Endothelialization of Intravascular Stents", *Journal of Interventional Cardiology*, presented in Coronary Stenting at the Thoraxcentre, Rotterdam, The Netherlands, 1986–1994, vol. 1, No. 2, 1988, pp. 25–36.
Ch.L. Zollifkofer, "Die Entwicklung endovaskulärer Stents", pp. 10–17.
E.P. Strecker et al., "Perkutan implantierbare, durch Ballon aufdehnbare flexible Tantal–Gefäss prothese", pp. 18–23.

Primary Examiner—Debra S. Brittingham
Attorney, Agent, or Firm—Fitch, Even, Tabin & Flannery

[57] ABSTRACT

A stent for transluminal implantation in hollow organs, in particular in blood vessels, ureters, oesophagae or gall tracts, comprising a substantially tubular body is described. The stent can be transformed from a compressed state with a first cross-sectional diameter into an expanded state with a second enlarged cross-sectional diameter. The wall of the tubular body has apertures which repeat both in the longitudinal direction and also in the peripheral direction of the stent and permit the expansion. Each aperture has at least one section which is arranged obliquely to the longitudinal axis of the stent, both in the compressed state and also in the expanded state of the stent.

32 Claims, 6 Drawing Sheets

STENT FOR THE TRANSLUMINAL IMPLANTATION IN HOLLOW ORGANS The present invention relates to a stent for the transluminal implantation in hollow organs, in particular in blood vessels, ureters, oesophagae or gall tracts, comprising a substantially tubular body which can be transformed from a compressed state with a first cross-sectional diameter into an expanded state with a second enlarged cross-sectional diameter, wherein the wall of the tubular body has apertures which repeat both in the longitudinal direction and also in the peripheral direction of the stent and permit the expansion.

Stents of this kind are used for the rechannelling of hollow organs changed by disease. For this purpose the stents are introduced in the compressed state via an insertion catheter to the point within the hollow organ which is to be treated, where they can be expanded through diverse measures to a diameter which corresponds to that of the healthy hollow organ so that a supportive action is achieved for the hollow organ, for example for the wall of a vessel.

One distinguishes between balloon expanded stents and self-expanding stents, depending on the manner in which the expanded state is achieved. Balloon expanded stents are installed in the compressed state on a special balloon catheter, are inserted up to the respective location to be treated of the hollow organ and are expanded there to the desired diameter by balloon insufflation. The stent retains its stability in the expanded state as a result of the plastic deformation of the stent material so that an adequate supportive action is achieved for the hollow organ. Self-expanding stents are held in a compressed state by auxiliary means, such as, for example, membrane-like covers, and are introduced via a catheter to the location to be treated within the hollow vessel. After removal of the cover these stents expand of their own accord through their inherent stress up to a pre-determined diameter within the hollow vessel so that the support of the wall of the hollow organ is achieved in this manner. Fundamentally these self-expanding stents can also be substantially pressed against the vessel wall with the aid of a balloon catheter.

The group of the self-expanding stents also include stents from the so-called "memory metal" Nitinol. Nitinol is a nickel-titanium alloy with a temperature dependent shape behaviour. If, for example, a Nitinol wire is given a specific shape and if the wire is subsequently heated beyond a specific "memory temperature" then this wire obtains the ability to recall this shape. If one subsequently cools the so treated wire down again below its conversion temperature, which is dependent on the alloy and on the heat treatment, then it becomes soft and easily deformable. On renewed heating beyond the conversion temperature the wire automatically readopts the impressed shape.

Self-expanding stents of the initially named kind are, for example, generated by cutting slots with a laser in the wall of a tubular body of a small diameter, with the slots extending parallel to the longitudinal axis of the body. These slots are arranged displaced relative to one another in the circumferential direction so that on an expansion of the tubular member, for example by balloon insufflation, or by heating in case of a stent of memory metal, diamond-like apertures arise which have longitudinal axes which likewise extend parallel to longitudinal axis of the tubular body. Stents of this kind have, however, the disadvantage that they only have a low flexibility both in the compressed state and also in the expanded state so that, on the one hand, the insertion into bent hollow vessels is only possible to a restricted extent, and on the other hand stents inserted into joint regions tend to kink which can lead to a reduction or interruption of the blood flow in the blood vessels or indeed to puncturing of the vessel wall.

Moreover, a shortening occurs in the longitudinal direction through the expansion of the stent, and this shortening is relatively uncontrolled so that the positioning of the stent at a specific location to be treated within the hollow organ can be relatively difficult.

The problem of low flexibility is solved in a known stent of this kind in that the connection between individual diamonds arranged adjacent to one another in the longitudinal direction of the stent is interrupted. The disadvantage of this arrangement is, however, that the free, pointed diamond ends project outwardly from the wall of the stent at the outer curve radius, in particular on bending of the stent, such as, for example, takes place during a curved implantation, and project into the inner region of the stent at the inner curve radius. This has the consequence that injury to the wall of the hollow organ and to the balloon of a balloon catheter that is used can occur. These are complications which cannot be accepted in practice.

The present invention is based on the object of providing a stent of the initially named kind which has a high flexibility both in the compressed state and also in the expanded state, and which simultaneously ensures a reliable, risk-free utilisation and in which no shortening arises through the expansion so that a problem-free positioning of the stent can be achieved.

This object is satisfied in accordance with the invention starting from a stent of the initially named kind in that each aperture has at least one section which is arranged obliquely to the longitudinal axis of the stent both in the compressed state of the stent and also in the expanded state of the stent.

Surprisingly, the flexibility of the stent can be significantly improved through the oblique arrangement of the apertures both in the compressed state and also in the expanded state relative to a stent with apertures which extend parallel to its longitudinal axis in the compressed state. Since it is possible in this way to dispense with separation of the connections between diamonds arranged alongside one another in the longitudinal direction no sharp edges exist in stents formed in accordance with the invention such as could cause injury to the wall of the hollow organ or to a balloon of a balloon catheter.

Furthermore, through the oblique arrangement of the apertures it is possible to counteract a tendency of the stent to shorten on expansion. Thus, when preparing a self-expanding stent of memory metal, for example, the stent is expanded from its compressed state by drawing it onto an expansion axle, with the usual shortening first arising. The diameter of the expansion axle is, in this arrangement, selected to be the same as the desired diameter of the stent in the expanded state.

Thereafter the stent, which is drawn onto the expansion axle is extended sufficiently until it has reached the desired length with the angle of inclination of a part of the oblique sections of the apertures being shortened. If the stent is heated in this state beyond the memory temperature, then it readopts this shape in which the shortening has been compensated after cooling below the conversion temperature and subsequent renewed heating. Normally, the desired length corresponds to the length of the stent in the compressed state in order to ensure precise positioning of the expanded stent during insertion.

In accordance with an advantageous form of the invention the apertures in the compressed state of the stent form slot-like openings in the wall of the tubular body. In this manner a particularly simple manufacture of the stent of the invention is possible since the slot-like openings can, for example, be cut in the tubular body by a laser. In principle, it is, however, also possible for the cut-outs, to already be made broader in the compressed state, which can, for example, be achieved by punching or erosion processes.

The apertures can be generated both in the compressed state of the stent and also in the expanded state of the stent. The generation in the compressed state is, however, advantageous since the material losses are lower when producing slot-like openings then when producing correspondingly expanded openings.

In accordance with a further advantageous embodiment the slot-like openings have a plurality of sections, in particular three sections, which are of zig-zag-like shape and which are respectively arranged obliquely to the longitudinal axis of the stent. In this way particularly uniform bending characteristics of the stent are achieved both in the compressed state and also in the expanded state.

In accordance with a further preferred embodiment of the invention the material of the wall of the tubular body lying between the apertures forms boundary elements for the apertures which can be dilated for the expansion of the stent. In this arrangement the confronting ends of boundary elements which are arranged adjacent to one another in the longitudinal direction are connected via intermediate elements which are in particular of V-shape. Through this design one achieves on the one hand a more flexible design of the stent formed in accordance with the invention. On the other hand the provision of separate intermediate elements brings about a decoupling between the boundary elements, which primarily ensure the expansion of the stent, and the intermediate elements, which are preferably used to compensate for the shortening.

Further advantageous embodiments of the invention are set forth in the subordinate claims.

Figure 2:
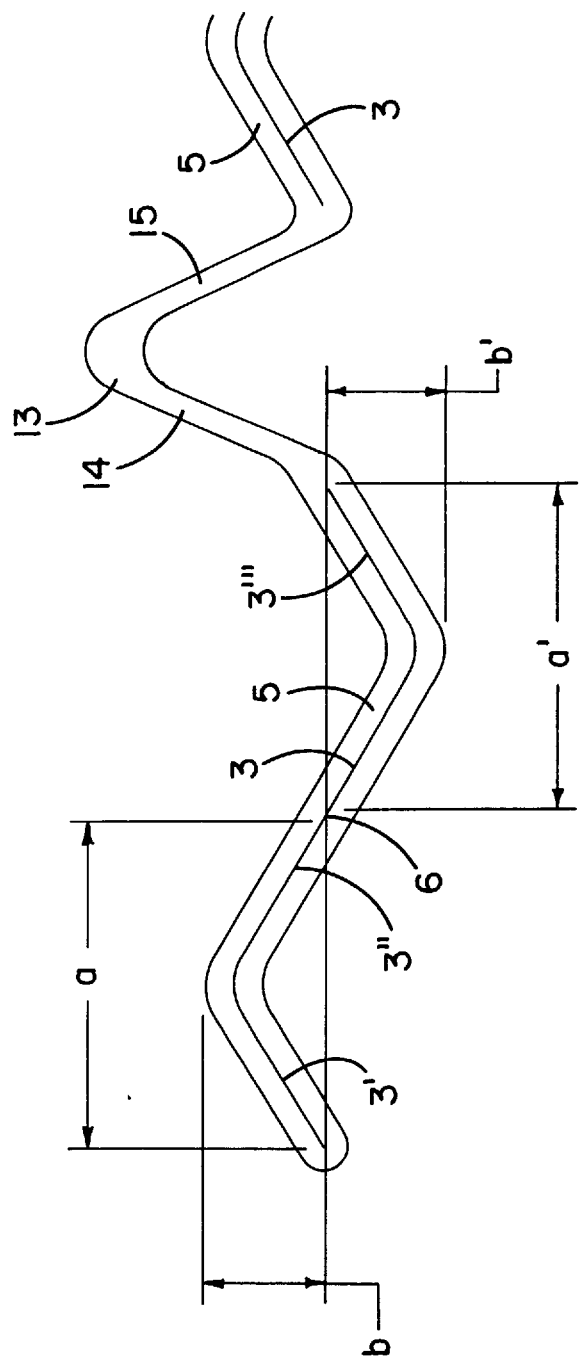
Figure 3A:
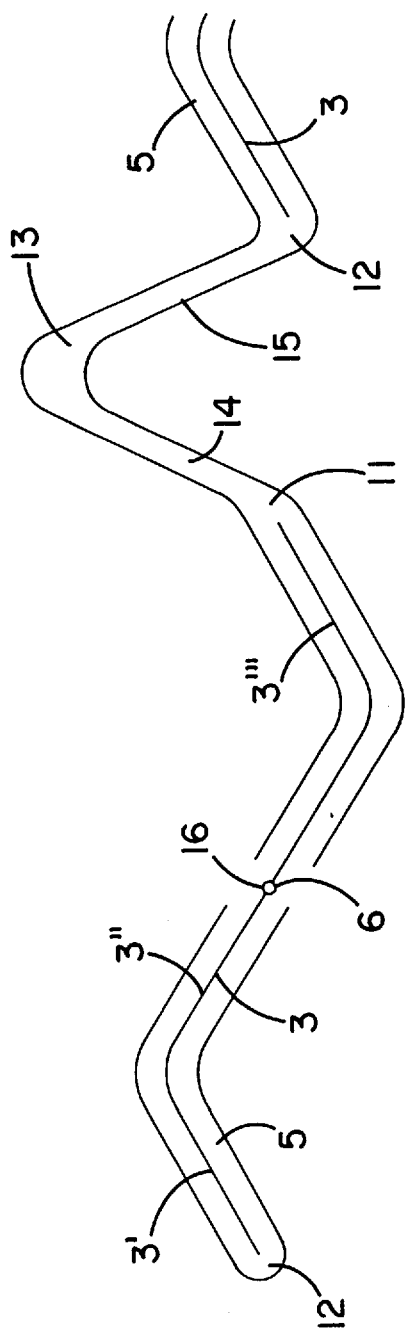
Figure 3B:
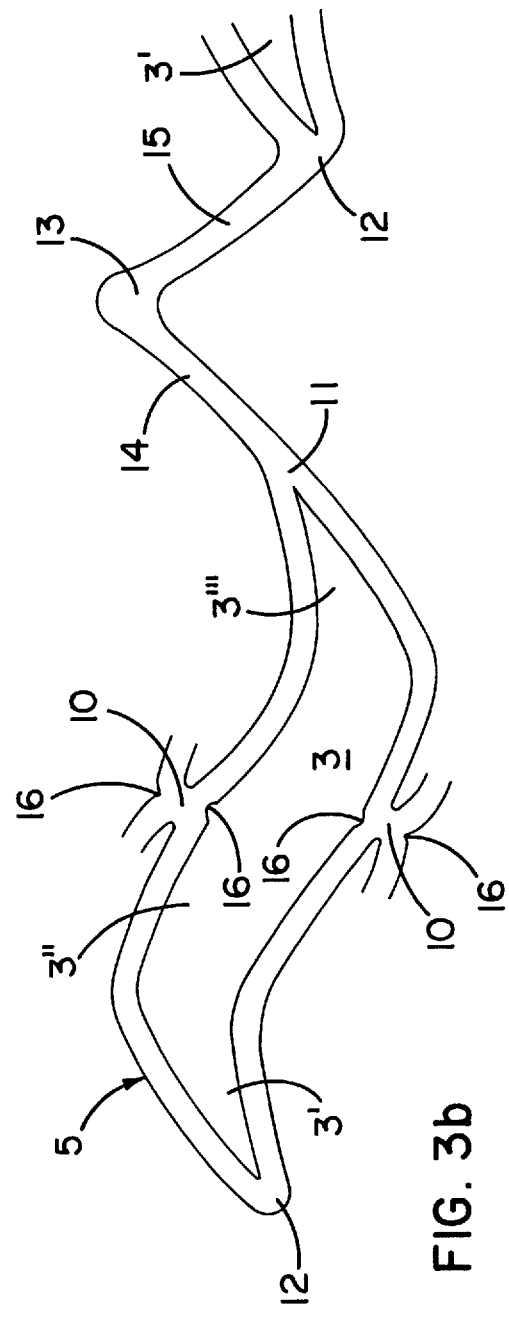
Figure 4A:
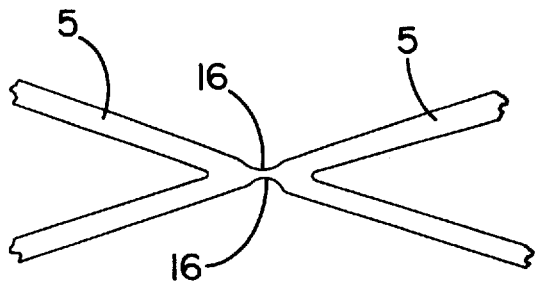
Figure 4B:
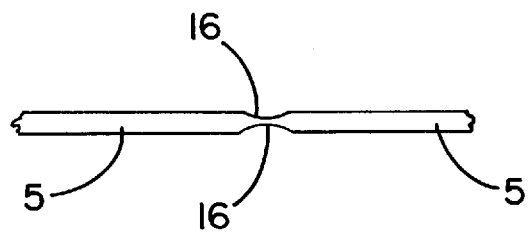
Figure 5:
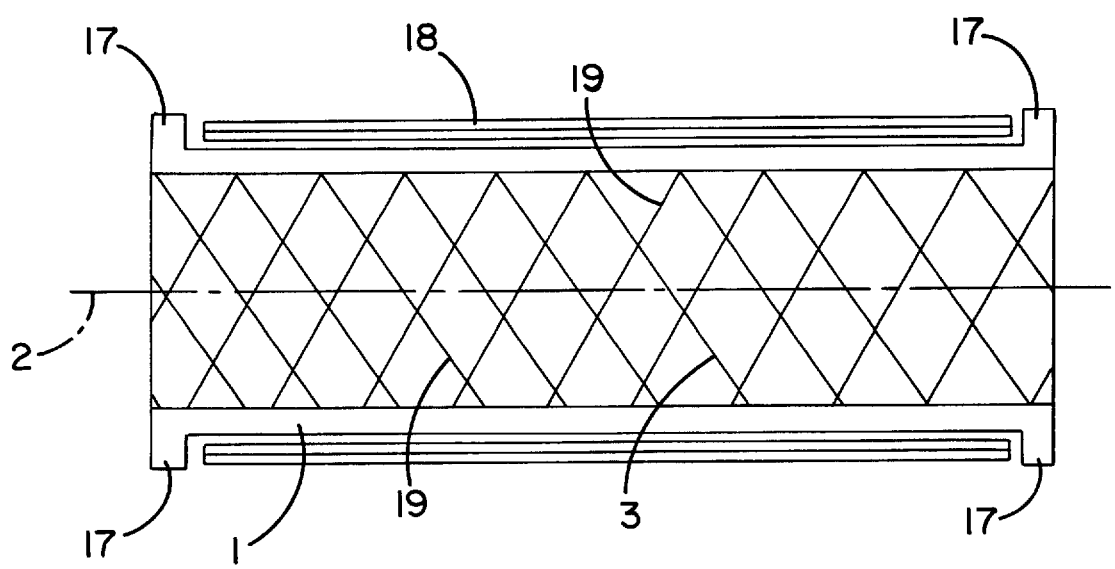

In the following the invention will be described in more detail with reference to an embodiment and to the drawings, in which are shown:

FIG. 1 a shortened cutting pattern shown flat for generating the apertures for a stent in accordance with the invention, FIG. 2 a detailed view in accordance with FIG. 1, FIGS. 3a–b the detailed view of FIG. 2 and also a detailed view corresponding thereto with a stent formed in accordance with the invention and in the expanded state, FIGS. 4a–b a further detailed view of a stent formed in accordance with the invention in the radial and tangential direction, FIG. 5 a schematic cross-section through a stent formed in accordance with the invention, and FIGS. 6 to 9 partial views of the grid structure of further embodiments of a stent formed in accordance with the invention.

FIG. 1 shows a cutting pattern such as is, for example, cut by means of a laser in the wall of a tubular body 1 (see FIG. 5) to produce a stent made in accordance with the invention. The course of the longitudinal axis of the tubular body 1 is provided with the reference numeral 2 in FIG. 1 in order to make the position of the cuts within the wall of the tubular body 1 clear Through the cutting process apertures 3, 4 arise in the wall of the tubular body 1 and have, in the compressed state, the shape of the slot-like openings illustrated in FIG. 1.

The slot-like openings 3 have three sections 3', 3", 3"' which are respectively arranged obliquely to the longitudinal axis 2 of the tubular body 1 and which in each case jointly form slot-like openings 3.

The material of the wall of the tubular body 1 lying between the apertures 3 forms respective boundary elements 5 which, as can be particularly well seen in FIG. 3b, respectively represent boundaries for the apertures 3.

The apertures 3 are made point-symmetrical relative to the symmetry points 6 which, together with the respective ends 7, 8 of the apertures 3, lie on lines parallel to longitudinal axis 2 of the tubular body 1. The point of symmetry 6 is thereby arranged in the center between the two ends 7, 8 of the apertures 3.

In each case two boundary elements 5 which are arranged adjacent to one another in the circumferential direction of the tubular body 1 (above one another in FIG. 1) are connected together via connection points 10 which are respectively arranged between the symmetry points 6 of the boundary elements 5.

The mutually adjacent ends 11, 12 of in each case two boundary elements arranged adjacent to one another in the longitudinal direction, are respectively connected to one another via V-shaped intermediate elements 13. The limbs 14, 15 of the intermediate elements 13 are respectively arranged obliquely to the longitudinal axis of the tubular body 1.

The apertures 3, 4, which are generated by the cutting pattern shown in FIG. 1, are uniformly distributed over the entire periphery of the tubular body 1 so that, for example, the boundary elements 5', 5" in FIG. 1 coincide.

Depending on the length of the tubular body 1 more or fewer V-shaped intermediate elements 13 and boundary elements 5 can be distributed along the longitudinal axis 2 of the tubular body 1 and are shown in FIG. 1. Accordingly the number of V-shaped intermediate elements 13 and of the boundary elements 5 can be varied along the circumference of the tubular body 1 depending on the circumference of the tubular body 1.

The point symmetrical layout of the slot-like openings 3 and thus of the boundary elements 5 can be particularly clearly seen from FIG. 2. The advantages of a stent in accordance with the invention are in particular achieved in that the geometrical spacings designated in the longitudinal direction by a and a' are of the same size as are the geometrical spacings b and b' in the circumferential direction of the tubular body 1.

It can be seen from FIG. 3 how the width of the boundary element 5 increases in the circumferential direction of the tubular body 1 by broadening of the apertures 3, whereby an expansion of the tubular body 1 is achieved. Furthermore, it can be seen from FIG. 3 that the longitudinal shortening of the boundary element 5 which occurs, and which can be recognised by the fact that the end 11 of the boundary 5 in FIG. 3b is displaced to the left relative to the position in FIG. 3a, is compensated for by a simultaneous broadening of the V-shaped intermediate element 13. In this way the positions of the end 12 of the neighbouring boundary element 5 in the compressed state (FIG. 3a) and in the expanded state (FIG. 3b) correspond. In this manner a unit consisting of a boundary element 5 and an intermediate element 13—and thus also the tubular body 1 as a whole—has the same length in the compressed state as in the expanded state in each case.

In the region of the connection locations 10 between two frame elements 5 arranged adjacent to one another in the circumferential direction of the tubular body 1 there are provided cut-outs 16 so that bending of the boundary elements 5 is facilitated at these locations. In this way the elastic characteristics of a stent of the invention are further improved.

The cut-outs 16 are shown in detail in FIG. 4 in the manner in which they can, for example, be provided between two directly connected together boundary elements 5. Corresponding cut-outs 16 can also be provided between the boundary elements 5 and the V-shaped intermediate elements 13.

In this arrangement both the cut-outs in the circumferential direction, as shown in FIG. 4a, and also the cut-outs in the radial direction, as shown in FIG. 4b, and also any further type of cut-outs are possible which favourably influence the flexibility of the stents formed in accordance with the invention.

In the cross-section of a stent 1 formed in accordance with the invention and schematically illustrated in FIG. 5 the apertures 3 are merely indicated by obliquely extending dashes 19. At its two ends the tubular body 1 has in each case thickened portions which extend radially outwardly, which are formed as projections 17 and extend in the circumferential direction. A resilient jacket 18 is provided between the projections 17, with the thickness of the jacket being substantially the same as the radial dimensions of the projecting parts of the projections 17 so that the stent has a substantially uniform outer surface. Furthermore, it can be seen from FIG. 5 that the inner surface of the tubular body 1 is made to extend uniformly.

The stent formed in accordance with the invention is preferably manufactured, prepared and used as follows:

The pattern of cuts shown in FIG. 1, and thus the slot-like openings 3, 4, are cut into the wall of a tubular body 1 consisting of memory metal using a laser. The diameter of the tubular body 1 is thereby so selected that it corresponds to the compressed state of the stent required for the implantation.

After the pattern of cuts shown in FIG. 1 has been cut over the entire length and the entire periphery of the tubular body 1, the tubular body 1 is drawn onto an expansion axle or mandrel, the diameter of which corresponds to the diameter of the stent required in the inserted expanded state. The cut-like openings 3, 4 are thereby broadened as shown in FIG. 3b. Thereafter, the tubular body drawn onto the expansion axle is extended in the longitudinal direction so such an extent that the shortening which arises through expansion is compensated for by bending open of the V-shaped intermediate elements 13, so that a surface structure arises consisting of boundary elements 5 and intermediate elements 13 as shown in FIG. 3b.

By heating the tubular body to above the memory temperature, the shape which has arisen is subsequently stored in the material.

After cooling down of the stent to below the conversion temperature, the stent can be pressed together to its starting diameter corresponding to the compressed state and covered with an elastic jacket 18 which consists, for example, of nylon, polyethylene, polyamide or polyurethane elastomers. An unintentional stripping of the resilient jacket 18 during implantation is prevented by the projections 17. At the same time the stent can be better observed through the projections 17 on the X-ray screen during insertion, so that a trouble-free positioning of the stent is ensured at the desired position within the hollow organ.

The stent is positioned at the desired location via an insertion catheter and an expansion of the stent is, for example, prevented by an additional sleeve or by a special catheter. By stripping off the sleeve or the catheter, the tubular body 1 adopts its stored shape as a result of the body temperature which lies above the conversion temperature. The length in the expanded state corresponds to the length of the stent in the compressed state as a result of the shortening compensation achieved via the intermediate elements 13 so that the position of the two ends of the stent observed on the X-ray screen during insertion is maintained.

As a result of the structure of the tubular body 1 in accordance with the invention, a high flexibility is achieved both in the compressed state and also in the expanded state so that an implantation is possible both in curve-shaped hollow organs as well as in hollow organs arranged in the vicinity of joints. A kinking of the stent by bending of the joint is extensively precluded by the high flexibility that is achieved. Moreover, a good longitudinal transverse stability of the stent is ensured both in the compressed state and also in the expanded state through the structure formed in accordance with the invention.

Furthermore, both the outer side and also the inner side of the tubular body are uniform and have in particular no elements with sharp edges which project outwardly or inwardly so that neither the hollow organ nor a balloon of a balloon catheter which eventually assists the expansion can be injured.

Apart from the described embodiment of memory metal, the advantages of a stent designed in accordance with the invention can also be achieved by using other materials such as, for example, tantalum, stainless steel or body-compatible plastics such as for example polyethylene, polyamide or polyurethane elastomers.

Figure 6:
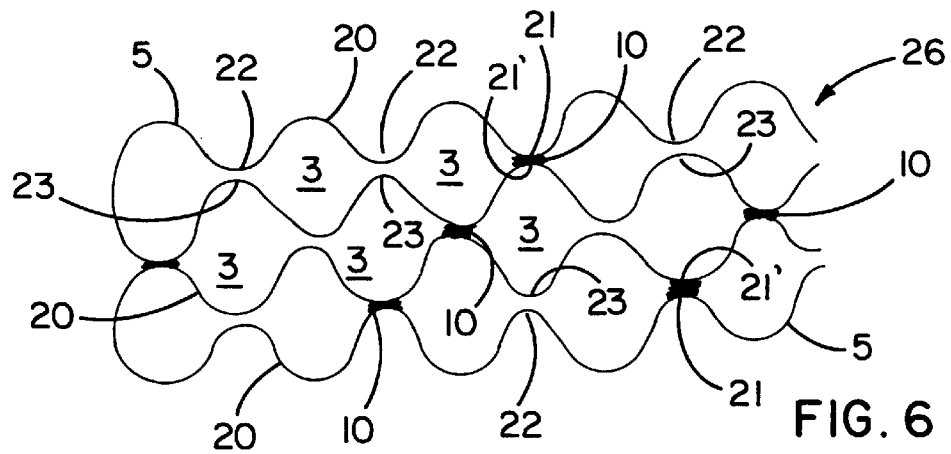

The grid structure 26 of a stent designed in accordance with the invention as shown in FIG. 6 consists of sinusoidal longitudinal components 20 which extend in the direction of the longitudinal axis of the stent and which form the boundary elements 5 and include the openings 3 between them. Respective longitudinal components 20 arranged alongside one another in the circumferential direction are connected to individual, mutually adjacent apex points 21, 21' via connection locations 10, whereas no connection exists between the remaining confronting apex points 22, 23.

The connection locations 10 between different apex points 21, 21' are arranged displaced relative to one another in the longitudinal direction of the stent. Through the displaced arrangement of the connection locations 10, and also through the non-connected, mutually displaceable apex points 22, 23, a good flexibility is achieved both in the longitudinal direction and also transverse to the longitudinal axis of the stent without producing sharp-edged elements. The stent can thereby consist of a self-expanding material, such as for example Nitinol, of stainless steel, of tantalum or of another suitable material.

Furthermore, the stent can be expanded to the desired diameter with or without balloon insufflation.

The stent has a good longitudinal stability and at the same time the tendency to kink in narrow curves is further reduced. Furthermore, it is possible to coat the grid structure with plastics, medications or textile braids for further applications, for example as endovascular prostheses for treating diseased broadened regions or defects.

Figure 7:
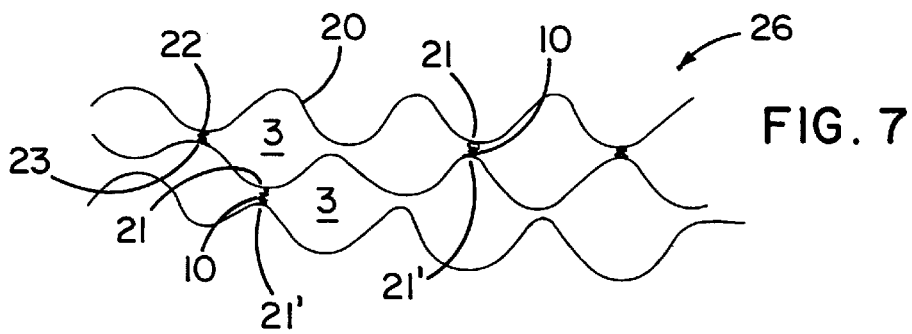

In the partial view of the grid structure 26 shown in FIG. 7, of a further embodiment of a stent formed in accordance with the invention, the connection locations 10 between the apex points 21, 21' are formed as connection webs.

Figure 8:
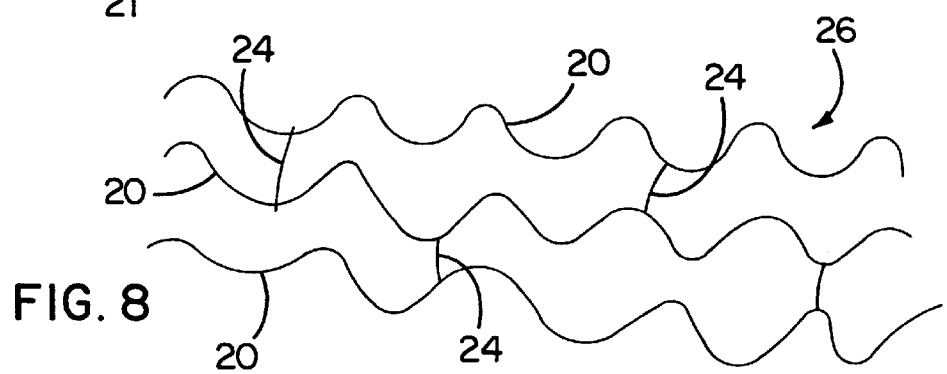

In the embodiment of FIG. 8 the sinusoidal longitudinal components 20 are arranged displaced relative to one another in the longitudinal direction, with the connections between the longitudinal components 20 arranged adjacent to one another in the circumferential direction taking place via pronounced connection bridges 24. The connection bridges 24 are thereby arranged at desired locations between the longitudinal components 20.

Figure 9:
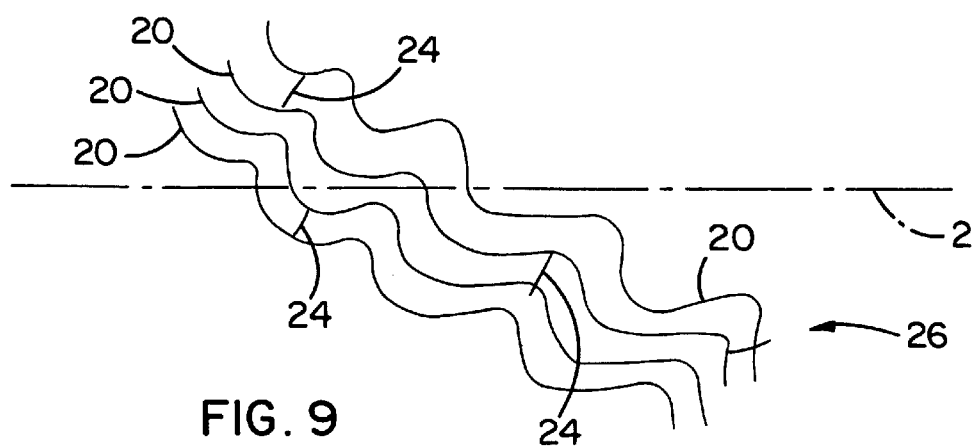

In the embodiment of FIG. 9, the longitudinal components 20 are arranged so that they extend obliquely to the longitudinal axis of the stent. In this way, a spiral arrangement of the longitudinal components 20 arises around the longitudinal axis 2 of the stent. Through this spiral arrangement the resilient deployment forces of the longitudinal components 20 are enhanced so that the stability of the stent in the expanded state can be further improved. Moreover, a sleeve arranged on the outer side of the stent, with which the stent is held in the compressed state during insertion, can be more easily drawn onto the already partly expanded stent again through rotation as a result of the spiral arrangement of the longitudinal components 20 so that the stent can be repositioned if it is unsatisfactorily positioned.

We claim:

1. A stent for transluminal implantation in hollow organs including blood vessels, ureters, oesophagae and gall tracts, the stent comprising:

a body having a substantially tubular wall with a longitudinal axis extending therethrough, the wall having a compressed state with a first cross-sectional diameter and an expanded state with a second cross-sectional diameter larger than the first cross-sectional diameter;

apertures of the body spaced in a longitudinal direction along the tubular wall and in a circumferential direction around the tubular wall for permitting the wall to expand from the compressed state to the expanded state, the apertures forming slot openings in the wall in the compressed state; and sections of the slot openings with each slot opening having a plurality of sections that extend obliquely relative to the longitudinal axis.

2. Stent in accordance with claims 1, characterized in that the sections of each of the slot openings form a substantially zig-zag pattern.

3. Stent in accordance with claim 1, characterized in that the sections of each of the slot openings form a pattern having a substantially z-shape.

4. Stent in accordance with claim 1, characterized in that the slot openings have a substantially sinusoidal shape.

5. Stent in accordance with claim 1, characterized in that the sections of each of the slot openings form a pattern having a substantially s-shape.

6. Stent in accordance with claim 1, characterized in that the sections form an angle with the longitudinal axis of the stent wall in the compressed state that is in the range of between 1° and 75°.

7. The stent of claim 6 wherein the range is between 10° and 45°.

8. Stent in accordance with claim 1, characterized in that the sections of each of the slot openings in the compressed state have a predetermined orientation so that the slot openings are symmetrical about a point in both the longitudinal and circumferential directions.

9. Stent in accordance with claim 8, characterized in that the slot openings each have spaced ends that are arranged on a line parallel to the longitudinal axis of the stent wall.

10. Stent in accordance with claim 9, characterized in that the point of symmetry of each slot opening is arranged on the line parallel to the longitudinal axis of the stent wall at the centre between the two ends of the slot openings.

11. Stent in accordance with claim 1, characterized in that the tubular wall of the body has portions lying between the slot openings which form boundary elements for the slot openings which can be dilated for the expansion of the stent wall.

12. Stent in accordance with claim 11, characterized in that the tubular wall includes boundary elements which are arranged adjacent to one another in the circumferential direction and a connecting web between the adjacent boundary elements.

13. Stent in accordance with claim 12, characterized in that the connecting web is disposed in the region of the centre between two ends of the boundary elements.

14. Stent in accordance with claim 11, characterized in that longitudinally adjacent boundary elements have respective ends that are connected to one another via resilient intermediate elements.

15. Stent in accordance with claim 14, characterized in that the intermediate elements each have sections which are arranged obliquely to the longitudinal axis of the stent wall.

16. Stent in accordance with claim 14, characterized in that the intermediate elements are V-shaped.

17. Stent in accordance with claim 14, characterized in that the connecting webs between the boundary elements and between the boundary elements and the intermediate elements are tapered in the radial and/or axial directions.

18. Stent in accordance with claim 12, characterized in that the connecting webs between the boundary elements are tapered in the radial and/or axial direction.

19. Stent in accordance with claim 1, characterized in that the tubular wall is manufactured from memory metal.

20. The stent of claim 19 whereas the memory metal comprises Nitinol.

21. Stent in accordance with claim 1, characterized in that the tubular wall is manufactured from a plastic compatible with the body.

22. The stent of claim 21 wherein the plastic is one of polyethylene, polyamide and polyurethane elastomers.

23. Stent in accordance with claim 1, characterized in that a resilient jacket is provided about the tubular wall.

24. Stent in accordance with claim 23, characterized in that the resilient jacket consists of plastic.

25. The stent of claim 24 wherein the plastic is one of polyethylene, polyamide and polyurethane elastomers.

26. Stent in accordance with claim 1, characterized in that the cross-sectional diameter of the tubular wall lies between 1 mm and 5 cm.

27. The stent of claim 26 wherein the cross-sectional diameter of the tubular wall lies between 3 mm and 3 cm.

28. The stent of claim 1 wherein the slot openings each comprise three sections that extend obliquely to the longitudinal axis.

29. A stent for transluminal implantation in hollow organs including blood vessels, ureters, oesophagae and gall tracts, the stent comprising:

a body having a substantially tubular wall with a longitudinal axis extending therethrough, the wall having a compressed state with a first cross-sectional diameter and an expanded state with a second cross-sectional diameter larger than the first cross-sectional diameter;

apertures of the body spaced in a longitudinal direction along the tubular wall and in a circumferential direction around the tubular wall for permitting the wall to expand from the compressed state to the expanded state the apertures forming slot openings in the wall in the compressed state; and sections of the slot openings with each slot opening having a plurality of sections that extend obliquely relative to the longitudinal axis, characterized in that at least one end of the tubular wall has a thicker portion extending in the circumferential direction.

30. Stent in accordance with claim 29, characterized in that the thicker portion projects outwardly in a radial direction.

31. A stent for transluminal implantation in hollow organs including blood vessels, ureters, oesophagae and gall tracts, the stent comprising:

a body having a substantially tubular wall with a longitudinal axis extending therethrough, the wall having a compressed state with a first cross-sectional diameter and an expanded state with a second cross-sectional diameter larger than the first cross-sectional diameter;

apertures of the body spaced in a longitudinal direction along the tubular wall and in a circumferential direction around the tubular wall for permitting the wall to expand from the compressed state to the expanded state, the apertures forming slot openings in the wall in the compressed state; and sections of the slot openings with each slot opening having a plurality of sections that extend obliquely relative to the longitudinal axis characterized in that a resilient jacket is provided about the tubular wall, and a radially outwardly directed thicker portion is provided at each end of the tubular wall and the resilient jacket is arranged between the radially projecting thicker portions.

32. Stent in accordance with claim 31, characterized in that the material thickness of the resilient jacket and the radial dimensions of the projecting thicker portion are of substantially the same size.

* * * * *